United States Patent [19]

Bayston et al.

[11] Patent Number: 6,118,032
[45] Date of Patent: Sep. 12, 2000

[54] PROCESS FOR THE PRODUCTION OF CYCLOPROPYLMETHYL HALIDES

[75] Inventors: Daniel John Bayston; Ronald Michael Scott; James Matthew Lovell, all of Oxfordshire; Lindsay Anne White, Leicestershire, all of United Kingdom

[73] Assignee: Eastman Chemical Company, Kingsport, Tenn.

[*] Notice: This patent issued on a continued prosecution application filed under 37 CFR 1.53(d), and is subject to the twenty year patent term provisions of 35 U.S.C. 154(a)(2).

[21] Appl. No.: 09/365,924

[22] Filed: Aug. 3, 1999

[51] Int. Cl.⁷ .............................. C07C 19/08; C07C 17/16
[52] U.S. Cl. ............................ 570/142; 570/261
[58] Field of Search ..................... 570/142, 261

[56] References Cited

U.S. PATENT DOCUMENTS

| 3,385,857 | 5/1968 | Mizzoni et al. . |
|---|---|---|
| 3,433,791 | 3/1969 | Bentley . |
| 3,474,101 | 10/1969 | Bentley . |
| 4,863,918 | 9/1989 | Gala et al. . |
| 5,288,932 | 2/1994 | Kaufhold . |
| 5,475,151 | 12/1995 | Liang et al. . |
| 5,502,257 | 3/1996 | Liang et al. . |

OTHER PUBLICATIONS

Beres, et al, Eur. J. Med. Chem.–Chim. Therap. 15, 571 (1980).

Lee et al, Can. J. Chem., 1980, 58, 1075–1079.

Corey et al, Tetrahedron Letters, 1972, 42, 4339–4342.

Primary Examiner—Alan Siegel
Attorney, Agent, or Firm—Michael J. Blake; Harry J. Gwinnell

[57] ABSTRACT

Disclosed is a process for the production of cyclopropylmethyl halides (CPMX) such as cyclopropylmethyl chloride (CPMCI) and cyclopropylmethyl bromide (CPMBr) wherein cyclopropanemethanol (CPMO) is contacted with a complex comprising a dialkyl sulfide and an N-halosuccinimide in the presence of an organic solvent.

5 Claims, No Drawings

PROCESS FOR THE PRODUCTION OF CYCLOPROPYLMETHYL HALIDES

This invention pertains to a process for the production of cyclopropylmethyl halides (CPMX) such as cyclopropylmethyl chloride (CPMCI) and cyclopropylmethyl bromide (CPMBr). The process involves contacting cyclopropanemethanol (CPMO) with a complex comprising an N-halosuccinimide and a dialkyl sulfide in the presence of an organic solvent. Distillation of the crude reaction product mixture gives the desired CPMX in good to excellent purity due to the formation of very small amounts of either halocyclobutanes or 1-halo-3-butenes which are difficult to separate from CPMX.

The preparation of cyclopropylmethyl halides by reacting CPMO with a phosphorus trihalide is described in *J. Med. Chem.-Chim. Therap.* 15, 571 (1980). The disclosed process requires very low temperatures, e.g. −650 to −80° C., in order to obtain acceptable selectivity to the desired CPMX. U.S. Pat. No. 3,385,857 describes a similar method for the preparation of CPMBr using diethyl ether as a solvent in order to achieve better recovery of the product. Again, the temperature used in the method was very low, e.g., −78° C. Published PCT Patent Application WO-97/30958 describes a process for the production of CPMX by reacting CPMO with excess chlorine or bromine in the presence of triphenylphosphine and dimethylformamide solvent. In order to obtain the desired products in high purity, large amounts of triphenylphosphine are required for the process. Also, the reaction is carried out under very dilute condition requiring the use of a large amount of dimethylformamide. The process of WO-97/30958 therefore results in poor throughput and the generation of large amounts of waste materials which make this process unattractive for commercial-scale production of CPMX.

U.S. Pat. No. 5,288,932 describes a process by a so-called onepot, two-step process in which CPMO is reacted with methanesulfonic acid halides in the presence of trialkylamines to form mesylates. The mesylates are decomposed thermally in the presence of the amine hydrohalide salts to generate the CPMX along with large amounts of amine-sulfonic acid salts. Such formation of large amounts of salts makes product isolation difficult and presents disposal and environmental problems. The process also requires a complicated and costly measurement and temperature control technique and presents difficulties of operating on a commercial scale. Lee at al, *Can. J. Chem.*, 1980, 58, 1075–79 discloses the reaction of CPMO with dilute, i.e., up to 2.0 Normal, aqueous hydrochloric acid at 60 or 85° C. for 1.5 to 10 hours. The reaction gave 10 to 13 products with cyclobutanol as the major product. Only trace amounts CPMCI were observed.

We have developed a simple and efficient process for the production of CPMX by contacting CPMO with a complex comprising an N-halosuccinimide and a dialkyl sulfide in the presence of an organic solvent. Corey, *Tetrahedron Letters*, 1972, 42, 4339, discloses the conversion of allylic and benzylic alcohols to the corresponding halides using a complex formed from dimethyl sulfide and an N-halosuccinimide. However, the use of the complex to convert alkanols to the corresponding alkyl halides has not been described in the literature. The present invention, therefore, provides a process for the preparation of a CPMX by contacting CPMO with a complex comprising an N-halosuccinimide and a dialkyl sulfide in the presence of an organic solvent. The process is especially useful for preparing cyclopropylmethyl chloride and bromide using a complex comprising N-chloro- or N-bromo-succinimide and a dialkyl sulfide as the halogenation agent. Cyclopropylmethyl halides are useful intermediates for the production of pharmaceuticals. See, for example, British Patent Publication GB 1,136,214, U.S. Pat. No. 3,433,791, Published PCT Patent Application WO 9304047, Spanish Patent ES 539110, U.S. Pat. No. 4,863,918, Czech Patent CZ 279821 and European Patent Publication EP 0380312 A1.

The amount of dialkyl sulfide/N-halosuccinimide complex used per mole of CPMO may be between about 0.9 and 1.8 moles complex, preferably between 1.0 and 1.2 moles complex, per mole CPMO. The dialkyl sulfide/N-halosuccinimide complex, a 1:1 complex of the 2 compounds, may be prepared according to known methods by contacting a dialkyl sulfide and an N-halosuccinimide in a solvent at a temperature of about 0 to 40° C., preferably about 0 to 10° C. Dialkyl sulfide and an N-halosuccinimide are reacted to produce the halogenation complex using a dialkyl sulfide:N-halosuccinimide more ratio of about 5:1 to 0.2:1. Although it is believed that dialkyl sulfides, e.g., dialkyl sulfides containing a total of from 2 up to about 12 carbon atoms, in general, may be used in the present invention, dimethyl sulfide is particularly preferred.

In accordance with the present invention, CPMO and the dialkyl sulfide/N-halosuccinimide complex are contacted in the presence of an organic solvent. Suitable process solvents include hydrocarbons such as pentane, hexane, heptane, benzene and toluene; chlorinated hydrocarbons such as dichloromethane, 1,2-dichloroethane, methyl chloroform, carbon tetrachloride, chlorobenzene, o-, m- and p-dichlorobenzene; dialkyl ethers such as t-butyl methyl ether, tetrahydrofuran; alkyl carboxylate esters such as methyl acetate and ethyl acetate; nitriles such as acetonitrile; dialkylsulfoxides such as dimethylsulfoxide; dialkylformamides such as dimethylformamide; dialkylacetamides such as dimethylacetamide; and the like. The preferred solvents are inert organic solvents such as dimethylformamide and, especially, dichloromethane which both have boilings points markedly different from the boiling point of the CPMX product and exhibit the highest selectivity for the product. Dichloromethane may be recovered by distillation and reused. The amount of solvent used can be varied substantially but normally will be in the range of about 5 to 30 volumes, preferably 10 to 20 volumes, solvent per volume of CPMO reactant.

CPMO and the dialkyl sulfide/N-halosuccinimide complex may be contacted in the presence of an organic solvent by adding, continuously or intermittently, CPMO or a solution of CPMO in the process solvent to an agitated mixture of the dialkyl sulfide/N-halosuccinimide complex in the process solvent. The complex may be wholly or partially soluble in the process solvent. Alternatively, the process may be carried out by adding the dialkyl sulfide to a mixture of CPMO and the N-halosuccinimide in an organic solvent. This alternative mode of operation is not preferred due to the non-selective reaction of the N-halosuccinimde alone with CPMO.

The process may be carried out at a temperature of about 0° C. up to the boiling point of the organic process solvent employed, preferably at a temperature of about 0° to 40° C. The process typically is carried out by adding the CPMO to the dialkyl sulfide/N-halosuccinimide complex in the process solvent at a temperature of less than about 20° C., preferably at a temperature of about 0 to 10° C. After addition of the CPMO is complete, the reaction temperature may be increased up to the boiling point of the solvent. However, when addition of the CPMO has been completed, it is preferred to heat the reaction mixture moderately, e.g., to a temperature of from about 20 to 40° C., to promote the halogenation. Pressure is not an important consideration and the process only is operated at ambient temperature although pressures moderately above or below ambient pressure may be used.

After completion of the reaction, the succinimide by-product may be removed from the crude reaction mixture by conventional liquid/solid separation techniques such as filtration. The organic reaction solution thus obtained is washed with an aqueous base solution such as sodium bicarbonate prior to distillation. The washed organic reaction solution then may be subjected to conventional fractional distillation to recover the CPMX product. The process of the present invention enables CPMX to be obtained in purities above 90%, usually above 95%, in yields above 60%, often above 65%.

The CPMO utilized in the present invention is readily obtained by the hydrogenation of cyclopropanecarboxaldehyde (CPCA) in the presence of a cobalt or nickel catalyst according to the process described in U.S. Pat. No. 5,475,151. The CPCA may be produced by the thermal isomerization of 2,3-dihydrofuran as is described in U.S. Pat. No. 5,502,257.

The processes provided by the present invention are further illustrated by the following examples. Gas chromatographic (GC) analyses were performed on a Hewlett-Packard 5890 series II gas chromatography with a 30 meter DB-Wax and a 30 meter DB-17 capillary columns. The identities of the products obtained were confirmed by nuclear magnetic spectrometry and gas chromatography-mass spectrometry by comparison to authentic samples. The percentages specified in the examples are by weight unless otherwise specified.

EXAMPLE 1

A solution of dimethyl sulfide (94.8 g, 1.53 mol, 1.1 equivalents—eq) in dichloromethane (200 mL, 2 volumes) was added dropwise under an atmosphere of nitrogen to a suspension of N-bromosuccinimide (271.5 g, 1.53 mol, 1.1 eq) in dichloromethane (800 mL, 8 volumes) while maintaining the temperature between 0 and 10° C. The resulting yellow suspension was stirred at 0–10° C. for 10 minutes. CPMO (100.5 g, 1.39 mol, 1.0 eq) was added dropwise to the yellow suspension while maintaining the temperature below 10° C. The reaction mixture was warmed to and maintained at 30° C. for 3 hours. GC analysis indicated that no starting material remained.

The orange suspension was cooled to 0° C., stirred at 0° C. for 1 hour and then filtered. The recovered was shown by proton NMR to be succinimide. The filtrate was washed with saturated aqueous sodium bicarbonate (500 mL, 5 volumes) and then with water (500 mL, 5 volumes) The organic phase then was distilled to provide CPMBr as an oil (126 g, 67% yield) having a purity of 98 area percent by GC analysis.

EXAMPLE 2

Dimethyl sulfide (15.5 g, 0.25 mol, 1.8 eq) was added dropwise under an atmosphere of nitrogen to a suspension of N-bromosuccinimide (37.1 g, 0.21 mol, 1.5 eq) in dimethylformamide (50 mL, 5 volumes) while maintaining the temperature between 0 and 10° C. The resulting yellow suspension was stirred at 0–10° C. for 30 minutes. CPMO (10 g, 0.139 mol, 1.0 eq) was added dropwise to the orange suspension while maintaining the temperature below 10° C. The reaction mixture was stirred at room temperature 20.5 hours after which GC analysis indicated that no starting material remained.

The solution was diluted with water (50 mL, 5 volumes) and then extracted twice with 100 mL portions (2×10 volumes) of pentane. The pentane solution was washed with water (2×50 mL, 2×5 volumes), dried over magnesium sulfate and filtered. The organic filtrate then was distilled to provide CPMBr as an oil (9.2 g, 49% yield) having a purity of 95 area percent by GC analysis.

EXAMPLE 3

A solution of dimethyl sulfide (4.74 g, 0.076 mol, 1.1 eq) in dichloromethane (10 mL, 2 volumes) was added dropwise under an atmosphere of nitrogen to a suspension of N-chlorosuccinimide (10.2 g, 0.076 mol, 1.1 eq) in dichloromethane (10 mL, 8 volumes) while maintaining the temperature between 0 and 10° C. The resulting yellow suspension was stirred at 0–10° C. for 15 minutes. CPMO (5 g, 0.06 mol, 1.0 eq) was added dropwise to the yellow suspension while maintaining the temperature below 10° C. The reaction mixture was warmed to and maintained at 30° C. for 18 hours. GC analysis indicated that 92 mole percent of the CPMO had been converted to CPMCl.

The invention has been described in detail with particular reference to preferred embodiments thereof, but it will be understood that variations and modifications can be effected within the spirit and scope of the invention.

We claim:

1. Process for the preparation of a cyclopropylmethyl halide (CPMX) which comprises contacting cyclopropanemethanol (CPMO) with a complex comprising an N-halosuccinimide and a dialkyl sulfide in the presence of an organic solvent.

2. Process according to claim 1 wherein halide is chloride or bromide, and halo is chloro or bromo, and the contacting is carried out at a temperature in the range of about 0 to 40° C.

3. Process for the preparation of a cyclopropylmethyl halide (CPMX) which comprises contacting cyclopropanemethanol (CPMO) with a complex comprising an N-halosuccinimide and dimethyl sulfide in the presence of an organic solvent wherein CPMO or a solution of CPMO in the process solvent is added to a mixture of the dimethyl sulfide/N-halosuccinimide complex in the process solvent.

4. Process according to claim 3 wherein CPMO or a solution of CPMO in the process solvent is added to an agitated mixture of the dimethyl sulfide/N-halosuccinimide complex in the process solvent at a temperature less than 20° C. and, when addition of the CPMO is complete, the reaction mixture is heat to a temperature of about 20 to 40° C.

5. Process according to claim 4 wherein the solvent is dichloromethane or dimethylformamide.

* * * * *